US00PP20443P2

(12) United States Plant Patent
Falstad, III

(10) Patent No.: US PP20,443 P2
(45) Date of Patent: Oct. 27, 2009

(54) ***HIBISCUS* PLANT NAMED 'SUMMER STORM'**

(50) Latin Name: ***Hibiscus* hybrid (L.)**
Varietal Denomination: Summer Storm

(75) Inventor: Clarence H. Falstad, III, Holland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 12/228,607

(22) Filed: Aug. 13, 2008

(51) Int. Cl.
*A01H 5/00* (2006.01)

(52) U.S. Cl. ..... Plt./257

(58) Field of Classification Search ..... Plt./257
See application file for complete search history.

*Primary Examiner*—Annette H Para

(57) ABSTRACT

A new and distinct cultivar of hardy *Hibiscus* hybrid plant named 'Summer Storm' with dark burgundy palmate leaves producing a multitude of pink blushed flowers with darker rose stripes and deep red eye over at least 12 weeks during the summer and early fall.

4 Drawing Sheets

Botanical classification: *Hibiscus* hybrid (L.).
Variety denomination: 'Summer Storm'.

SUMMARY, BACKGROUND AND ORIGIN OF THE PLANT

The present invention relates to the new and distinct hardy *hibiscus* plant, *Hibiscus* 'Summer Storm' hybridized by Clarence H. Falstad in the summer of 2004 at a nursery in Zeeland, Mich. The Plant is a cross between *Hibiscus* 'Kopper King' U.S. Plant Pat. No. 10,793 (female parent) times 'Fireball' U.S. Plant Pat. No. 13,631. *Hibiscus* 'Summer Storm' has been propagated both by stem cuttings and tissue culture at the same nursery in Zeeland, Mich. The resultant plants have been found to be stable and true to type in successive generations of asexual reproduction.

*Hibiscus* 'Summer Storm' differs from its parents as well as all other hardy *hibiscus* known to the applicant in many traits. The foliage color of 'Summer Storm' is a deeper darker burgundy than 'Kopper King' which is darker than 'Fireball'. The foliage shape of 'Summer Storm' is variable, depending on the time of year and position on the stem, but in general the texture is less coarse or more finely dissected than 'Kopper King' and less dissected than 'Fireball'. The flowers of 'Summer Storm' are most similar to 'Kopper King' but the new plant has deeper rose color in the background and more intense veining. The flowering season of 'Summer Storm' starts about the same time as 'Kopper King' but extends four to six weeks longer depending on when ceased by frost or prolonged cold weather and short days. The branching of 'Summer Storm' is greater than 'Kopper King' and more like that of 'Fireball'. The stem branch angle of the new plant is more upright than 'Fireball', whereas in 'Kopper King' there are few if any branches.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

GENERAL DESCRIPTION OF THE PLANT

Figure 1:
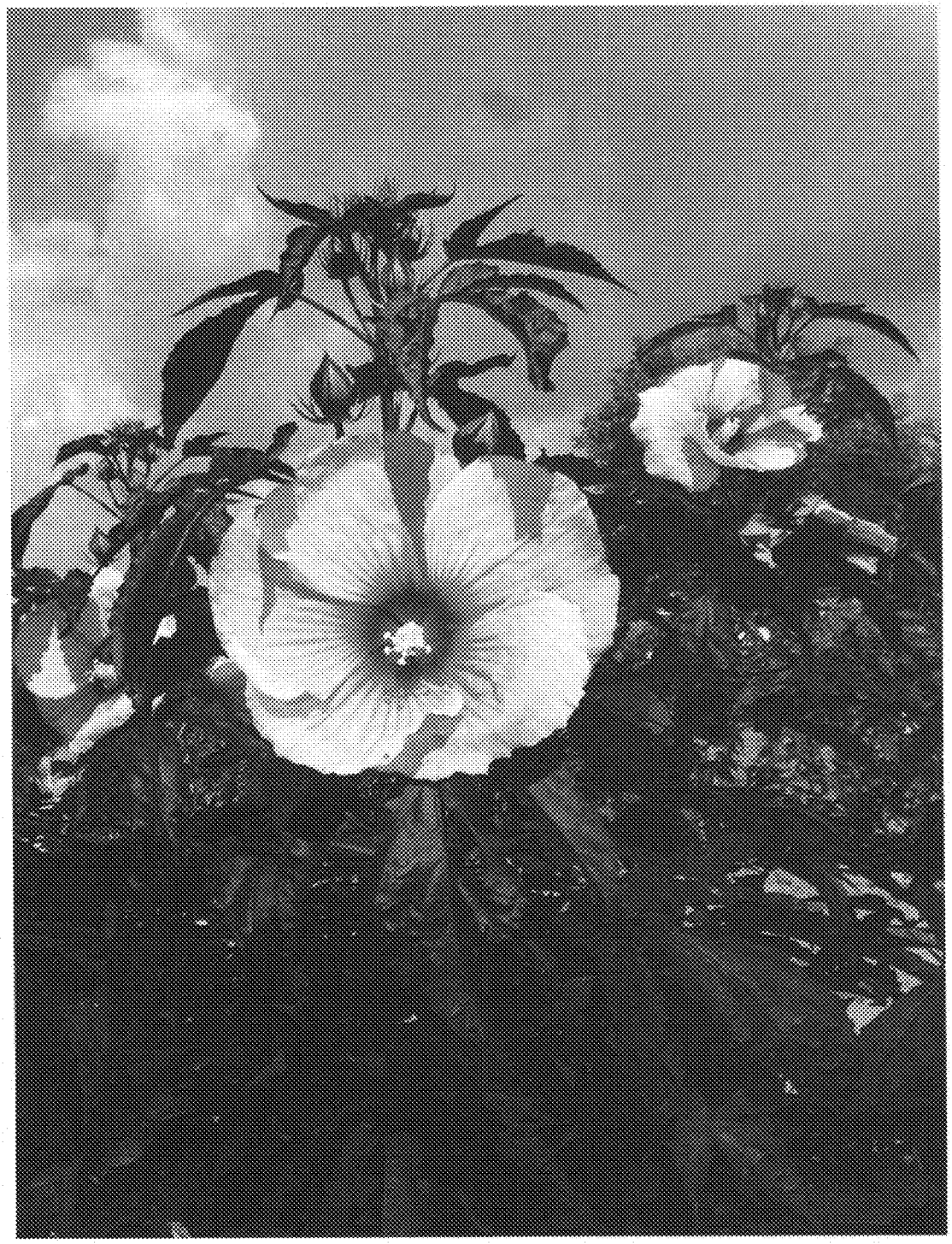
FIG. 1 shows the plant in full flower.
Figure 2:
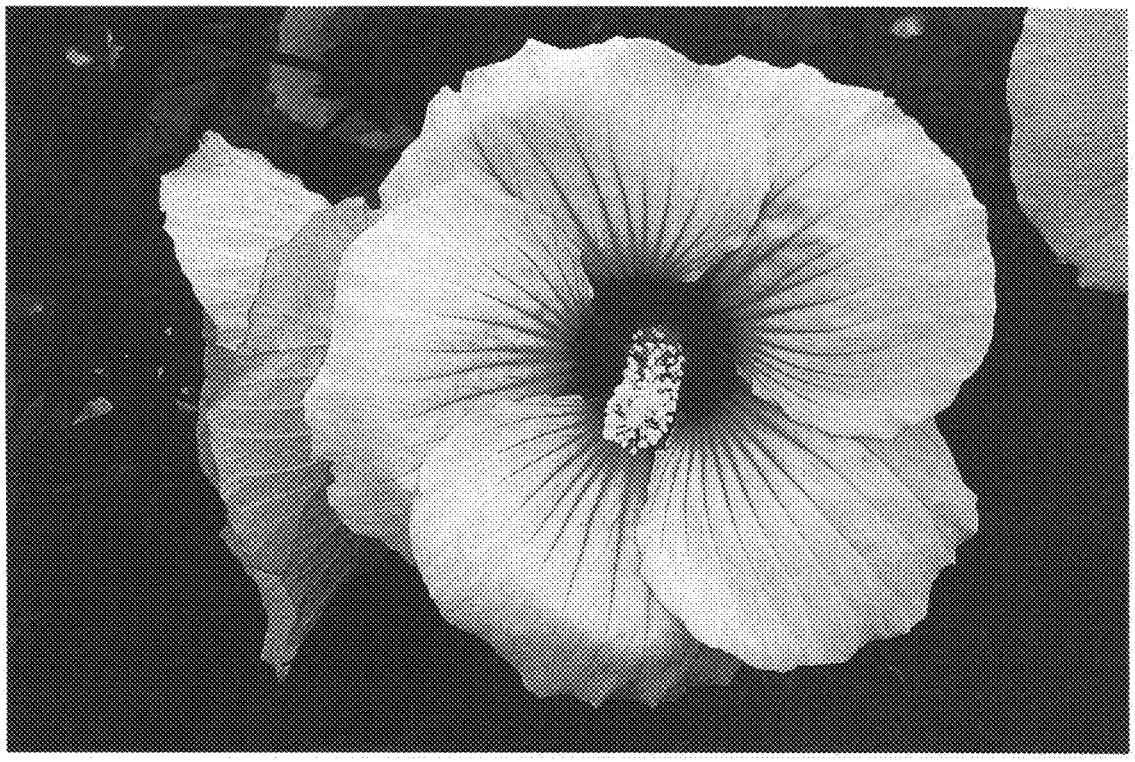
FIG. 2 shows a close-up of the flower.
Figure 3:
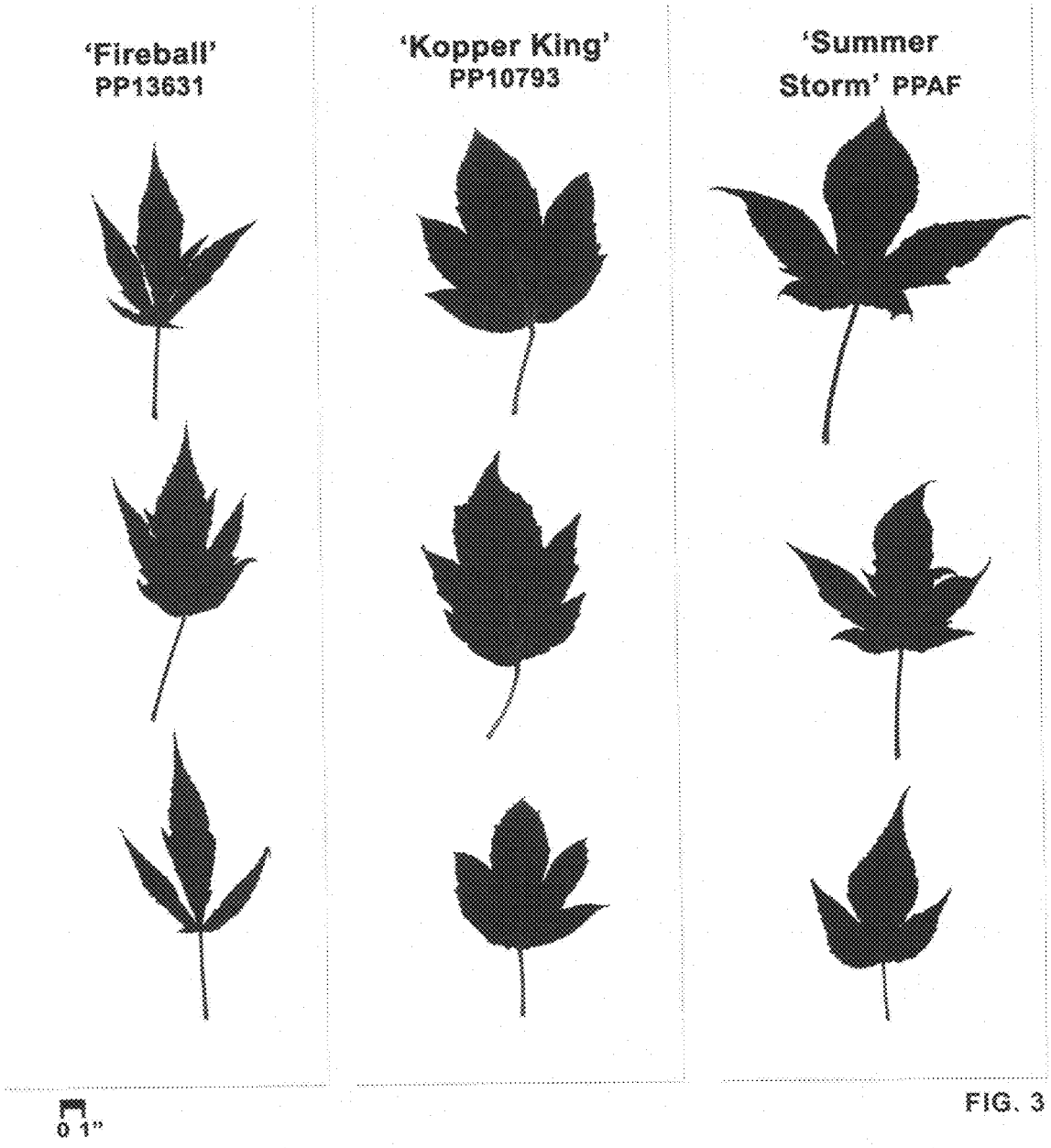
FIG. 3 shows dissected leaf form variation and colors in comparisons to both parents.
Figure 4:
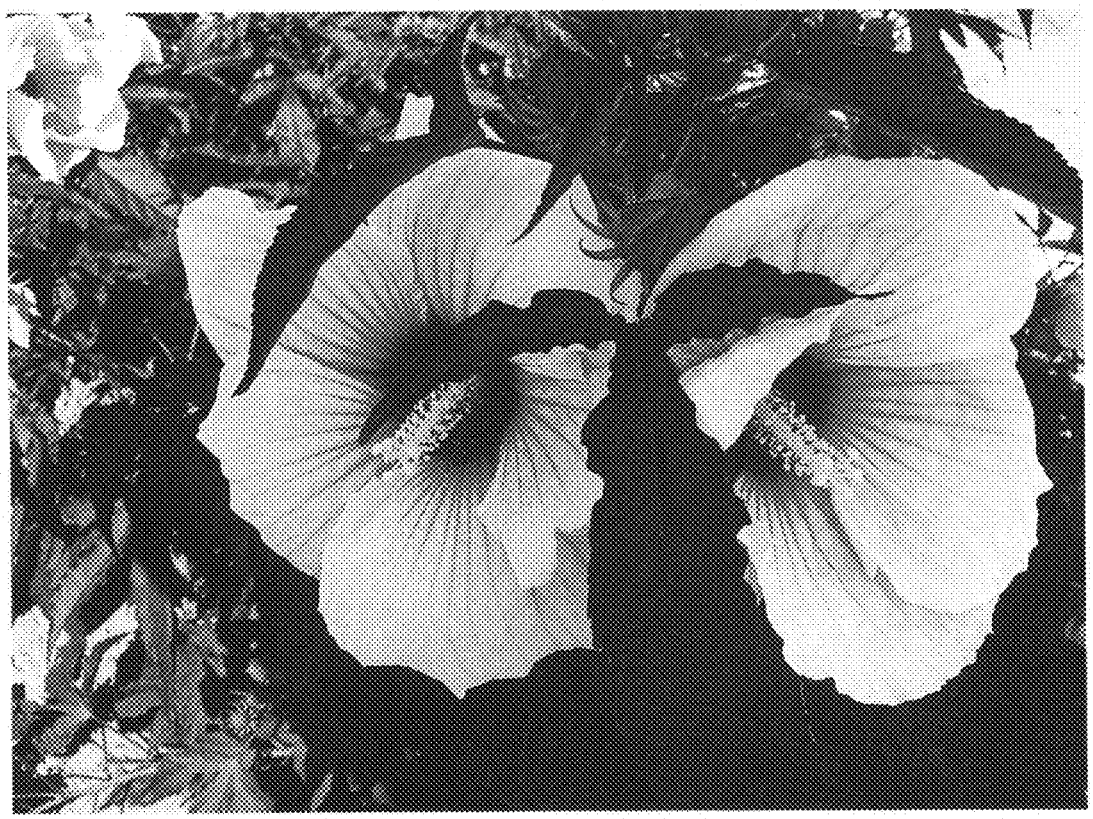
FIG. 4 shows close up of the flower, buds and foliage color.

*Hibiscus* 'Summer Storm' differs from *hibiscus* cultivars known to the inventor in that it has:

1. Intense, dark burgundy foliage with red petioles;
2. Compact habit with heavy branching of dark reddish purple stems;
3. Pink blush to rose petals with darker veining in long flowering season;

DETAILED BOTANICAL DESCRIPTION

The following descriptions and color references are based on the 2001 edition of The Royal Horticultural Society Colour Chart except where common dictionary terms are used. The new plant, *Hibiscus* 'Summer Storm', has not been observed under all possible environments. The phenotype may vary slightly with different environmental conditions, such as temperature, light, fertility, moisture and maturity levels, but without any change in the genotype. The following observations and size descriptions are of a two-year old plant in the trial field of a nursery in Zeeland, Mich. with supplemental fertilizer and water as needed. The plants were not treated with grow regulators.

Botanical classification: *Hibiscus* L.×hybrid.

Parentage: Hybrid of *Hibiscus* 'Kopper King' U.S. Plant Pat. No. 10,793 (female) times *Hibiscus* 'Fireball' U.S. Plant Pat. No. 13,631 (male).

Propagation:

*Method.*—Stem cuttings and sterile laboratory tissue culture division.

*Time to initiate roots from tissue culture.*—About two weeks.

*Rooting habit.*—Normal, thick to about 4 cm diameter, fleshy, branching; root color white depending on soil type.

Plant description:

*Plant shape and habit.*—Hardy herbaceous perennial with 10 to 18 thick upright branched main stems producing rounded mound; up to 15 branches per main stem protruding at 45° to 60° angle from vertical.

*Crop time.*—Under normal summer growing conditions 12 to 18 weeks to flower in a four-liter container. Plant vigor is very good.

*Plant size.*—Unpinched plant stems 137 to 162 cm tall, average about 148 cm tall from soil line, overall plant 190 to 210 cm wide at the widest point; spring season pinched plant stems 130 to 160 cm, average about 140 cm, tall from soil line and 120 to 160 cm wide at the widest point.

*Internode length.*—Unpinched plant about 9 cm; pinched plant about 7 cm.

*Foliage description.*—Opposite; dentate; glabrous; shiny above and glaucous below; leaf shape is variable tri-lobed to five-lobed, deeply to moderately incised, with the center lobe the largest; largest leaves 20 cm long and 25 cm wide; average leaves about 6.5 cm long and 6.5 cm wide; between RHS 187A and RHS N187A with palmate veins between RHS 187B and RHS 187C on the top surface; bottom surface closest to RHS 138A with tinting around the margin of RHS 187A and main veins nearest RHS 186D and smaller veins near perimeter of RHS 185 A; lower leaves shaded by new foliage show mottled tinting of RHS 187 A and more green RHS 146B on the top surface with veins of RHS 187A and RHS 187B; bottom surface of lower leaves between RHS 138A and RHS 138B with veins closest to RHS 138D; fall color develops closest to RHS 44B.

*Petioles.*—5 to 10 cm long and 4 mm wide; plano-convex, cylindrical with the top portion flattened; between RHS 187B and RHS 187C on top and between RHS 179B and RHS 179C on the bottom of the upper leaves; RHS 187A on the top and closest to RHS 177B on the bottom on the lower leaves of the plant.

Flower description:

*Buds one day prior to opening.*—Approximately 6.5 cm long and 3 cm in diameter, acute apex and bluntly rounded base, unopened petals R.H.S. between RHS 65A and RHS 65B with tinting of RHS 64B producing an overall effect of RHS 64D; prior to showing petals buds are about 3 cm long and 2.5 cm in diameter, ovoid with acute apex; color between RHS 144A and RHS 144B with veins RHS 144A and accents on the veins or tips of RHS N187A.

*Epicalyx.*—Entire, smooth, glabrous, linear with sharply acute apex; 10 to 14 per flower; 2.2 cm long tapering to base of 3 mm wide; RHS 144A on both inner and outer surface with slight tinting of tips RHS N186A.

*Sepals.*—5, fused in lower half forming tubular star-shaped calyx; acute apex; about 3.5 cm long and 1.7 cm wide; RHS 144C and tinted on veins and margins with RHS 59A.

*Flowers.*—Solitary, 24 to 36 per main scape without pinching, 10 to 14 on terminal stems on pinched plants; flat, upward and outwardly facing; 20 to 22 cm across, smaller later in flowering season; persist for a one to two days; effective for at least 12 weeks beginning mid July and lasting into October, beginning about one week later if pinched; no detectable fragrance.

*Petals.*—Five; adnate to the androecium, imbricate to about 80% overlapping at widest part (only 20% of each petal not being overlapped by the two petals on either side).

*Gynoecium.*—Style: enclosed in column; white, 7 to 9 cm long and 2 to 3 mm diameter; split into five branches in the distal 12 to 15 mm.

*Stigma.*—Five; about 2 mm in diameter, lighter than RHS 36D.

*Androecium.*—Filaments: numerous, about 120; less than 1 mm in diameter and about 5 mm long; attached to nearly the entire length of column; RHS 62C and deeper pink, RHS 64D toward base of column.

*Anthers.*—Reniform; about 2 mm long and 1 mm wide; nearest RHS 11D.

*Pollen.*—Numerous, less than 0.1 mm long, nearest RHS 11D.

*Pedicel.*—From base of sepal to abscission point about 2.5 cm long and 3 mm wide on early flowers, RHS N186A with undertones of RHS 138C.

*Peduncle.*—Flowers are held out easily visible by up to 12 cm long from abscission point to stem and 3 mm wide on early flowers shortening to about 6 cm higher on stem, nearest RHS 59A.

*Fruit.*—Loculicidal capsule; glabrous; globose, occasionally with abruptly acute apex; RHS N199B when mature.

*Seed.*—Floccose, globose to slightly reniform; 3 to 4 mm in diameter; RHS 200A.

Disease resistance: Resistance beyond that of other hardy *hibiscus* cultivars has not been observed. The plant grows best with plenty of moisture and adequate drainage, but is able to tolerate some drought when mature. Hardiness at least from USDA zone 4 through 9, and other disease resistance is typical of that of other *hibiscus* cultivars.

I claim:

1. A new and distinct cultivar of hardy *Hibiscus* hybrid plant named 'Summer Storm' as herein described and illustrated, with dark burgundy palmate leaves and producing a multitude of pink blushed flowers with darker rose stripes and deep red eye over at least 12 weeks during the summer and early fall, and suitable as a potted plant, for the garden, and for cut flower arrangements.

* * * * *